US010197793B2

(12) United States Patent
Liu et al.

(10) Patent No.: US 10,197,793 B2
(45) Date of Patent: Feb. 5, 2019

(54) LIGHT MODULATOR USING TOTAL INTERNAL REFLECTION AT AN INTERFACE WITH A TUNABLE CONDUCTIVE LAYER

(71) Applicant: The Chinese University of Hong Kong, Shatin, N.T., Hong Kong SAR (CN)

(72) Inventors: Xudong Liu, Foshan (CN); Zefeng Chen, ChaoZhou (CN); Edward Philip John Parrott, Hung Hom (HK); Benjamin Ung, Evandale (AU); Jianbin Xu, Hong Kong (CN); Emma MacPherson, Sai Kung (HK)

(73) Assignee: The Chinese University of Hong Kong, Shatin, N.T. (HK)

( * ) Notice: Subject to any disclaimer, the term of this patent is extended or adjusted under 35 U.S.C. 154(b) by 0 days.

(21) Appl. No.: 15/589,936

(22) Filed: May 8, 2017

(65) Prior Publication Data
US 2017/0329127 A1    Nov. 16, 2017

Related U.S. Application Data

(60) Provisional application No. 62/335,485, filed on May 12, 2016.

(51) Int. Cl.
*H04B 10/00* (2013.01)
*G02B 26/08* (2006.01)
(Continued)

(52) U.S. Cl.
CPC ............ *G02B 26/0816* (2013.01); *G01J 3/42* (2013.01); *G01J 5/08* (2013.01); *G01N 21/3581* (2013.01);
(Continued)

(58) Field of Classification Search
USPC .................................................. 398/182–191
See application file for complete search history.

(56) References Cited

U.S. PATENT DOCUMENTS 5,011,250 A * 4/1991 Okada ..................... G02F 1/377
359/332
5,067,788 A * 11/1991 Jannson ................... G02B 6/34
385/123
(Continued)

FOREIGN PATENT DOCUMENTS

EP         2597509 A1    5/2013

OTHER PUBLICATIONS

Chen et al., "Experimental Demonstration of Frequency-Agile Terahertz Metamaterials," Nature Photonics, vol. 2, May 2008, 295-298.
(Continued)

*Primary Examiner* — Agustin Bello
(74) *Attorney, Agent, or Firm* — Kilpatrick Townsend & Stockton, LLP

(57) ABSTRACT

A light modulator (e.g., for terahertz radiation) may be constructed using a prism in which light undergoes total internal reflection (TIR) at one surface. A tunable conductive layer is disposed on the TIR surface. The tunable conductive layer can have a conductivity that is dynamically controllable, e.g., by applying a voltage across the tunable conductive layer or by optically pumping the tunable conductive layer. The tunable conductive layer can absorb a portion of the reflected light beam, attenuating the beam, with the attenuation being a function of the electrical conductivity of the tunable conductive layer. The phase of the reflected light beam can also be altered as a function of electrical conductivity of the tunable conductive layer.

25 Claims, 17 Drawing Sheets
(6 of 17 Drawing Sheet(s) Filed in Color)

(51) Int. Cl.

| | |
|---|---|
| *G01N 21/3581* | (2014.01) |
| *G02F 1/315* | (2006.01) |
| *G01J 3/42* | (2006.01) |
| *G01J 5/08* | (2006.01) |
| *H01Q 15/00* | (2006.01) |
| *G02F 1/01* | (2006.01) |

(52) U.S. Cl.
CPC ............... *G02F 1/01* (2013.01); *G02F 1/315* (2013.01); *H01Q 15/0006* (2013.01)

(56) References Cited

U.S. PATENT DOCUMENTS

| | | | | |
|---|---|---|---|---|
| 5,157,537 | A * | 10/1992 | Rosenblatt | G02F 1/01 359/245 |
| 5,157,541 | A * | 10/1992 | Schildkraut | G02F 1/195 359/245 |
| 5,212,583 | A * | 5/1993 | Vali | G02F 1/29 359/245 |
| 5,337,183 | A * | 8/1994 | Rosenblatt | G02F 1/01 359/245 |
| 5,570,139 | A * | 10/1996 | Wang | G02F 1/195 345/84 |
| 5,986,808 | A * | 11/1999 | Wang | G02B 27/288 349/106 |
| 6,208,422 | B1 * | 3/2001 | Naya | G01N 21/553 356/445 |
| 6,529,277 | B1 * | 3/2003 | Weitekamp | B82Y 10/00 356/445 |
| 6,618,204 | B2 * | 9/2003 | Takatori | B82Y 20/00 345/32 |
| 6,798,521 | B2 * | 9/2004 | Elkind | G01N 21/553 356/445 |
| 6,885,454 | B2 * | 4/2005 | Naya | G01N 21/553 356/134 |
| 6,982,819 | B2 * | 1/2006 | Sawin | B82Y 20/00 359/245 |
| 7,057,786 | B2 * | 6/2006 | Sawin | B82Y 20/00 345/87 |
| 7,615,739 | B2 * | 11/2009 | Berman | B82Y 35/00 250/216 |
| 8,009,356 | B1 * | 8/2011 | Shaner | G02B 27/56 359/288 |
| 8,263,964 | B2 * | 9/2012 | Yu | B82Y 10/00 257/9 |
| 8,355,199 | B1 * | 1/2013 | Robertson | G02B 6/29341 359/245 |
| 8,554,083 | B2 * | 10/2013 | Breunig | H04B 10/2575 398/157 |
| 8,655,114 | B2 * | 2/2014 | Popovic | G02B 6/12007 385/1 |
| 2004/0223159 | A1 * | 11/2004 | Iwata | G01N 21/253 356/445 |
| 2005/0248829 | A1 * | 11/2005 | Sawin | B82Y 20/00 359/321 |
| 2005/0248830 | A1 * | 11/2005 | Sawin | B82Y 20/00 359/321 |
| 2008/0137068 | A1 * | 6/2008 | Ouchi | G01N 21/3581 356/51 |
| 2009/0040507 | A1 * | 2/2009 | VanWiggeren | G01N 21/553 356/73 |
| 2009/0141376 | A1 * | 6/2009 | Smith | G01N 21/553 359/833 |
| 2009/0195783 | A1 * | 8/2009 | Tazuke | G01N 21/553 356/445 |
| 2009/0213384 | A1 * | 8/2009 | Naya | B82Y 20/00 356/450 |
| 2010/0213375 | A1 * | 8/2010 | Loeffler | G02F 1/39 250/339.07 |
| 2011/0085170 | A1 * | 4/2011 | Yen | G01N 21/554 356/445 |
| 2011/0103801 | A1 * | 5/2011 | Breunig | H04B 10/2575 398/118 |
| 2011/0114856 | A1 | 5/2011 | Cooke | |
| 2012/0148252 | A1 * | 6/2012 | Turchinovich | B82Y 20/00 398/116 |
| 2013/0240734 | A1 * | 9/2013 | Booksh | G01N 21/553 250/339.11 |
| 2013/0242298 | A1 * | 9/2013 | Miyaura | G01N 21/553 356/246 |
| 2015/0086150 | A1 * | 3/2015 | Ouchi | G02F 1/3511 385/2 |
| 2015/0212388 | A1 * | 7/2015 | Ouchi | G02F 1/3534 359/326 |
| 2015/0316832 | A1 * | 11/2015 | Sato | G01J 3/10 250/338.1 |
| 2016/0069673 | A1 * | 3/2016 | Takayanagi | G01B 11/0641 250/339.11 |
| 2017/0059963 | A1 * | 3/2017 | Ouchi | G01N 21/3586 |
| 2017/0329127 | A1 * | 11/2017 | Liu | G02B 26/0816 |
| 2017/0336259 | A1 * | 11/2017 | Kawada | G01J 3/14 |
| 2018/0052186 | A1 * | 2/2018 | Su | G01Q 30/02 |

OTHER PUBLICATIONS

Chen et al., "A Metamaterial Solid-State Terahertz Phase Modulator," Nature Photonics, vol. 3, No. 3 (2009): 148-151.
Chen et al., "Active Terahertz Metamaterial Devices," Nature, vol. 444, Nov. 30, 2006, 597-600.
Degl'Innocenti et al., "Low-Bias Terahertz Amplitude Modulator Based on Split-Ring Resonators and Graphene," ACSNANO, vol. 8, No. 3, 2014, 2548-2554.
Gao et al., "High-Contrast Terahertz Wave Modulation by Gated Graphene Enhanced by Extraordinary Transmission Through Ring Apertures," Nano Letters, 2014, 14, 1242-1248.
Lee et al., "Switching Terahertz Waves with Gate-Controlled Active Graphene Metamaterials," Nature Materials, vol. 11, Nov. 2012, 936-941.
Liu et al., "Graphene Based Terahertz Light Modulator Reflection Geometry," Advanced Optical Materials, 2017, 1600697, 7 pages.
Liu et al., Exloiting Total Internal Reflection Geometry for Efficient Optical Modulation of Terahertz Light, APL Photonics, 1, 076103 (2016), 7 pages.
Miao et al., "Widely Tunable Terahertz Phase Modulation with Gate-Controlled Graphene Metasurfaces," Phys. Rev. X 5, 041027, (2015), 13 pages.
Shi et al., Optimizing Broadband Terahertz Modulation with Hybrid Graphene/Metasurface Structures, Nano letters 15, No. 1 (2014): 372-377.

* cited by examiner

LIGHT MODULATOR USING TOTAL INTERNAL REFLECTION AT AN INTERFACE WITH A TUNABLE CONDUCTIVE LAYER

CROSS-REFERENCE TO RELATED APPLICATIONS

This application claims the benefit of U.S. Provisional Application No. 62/335,485, filed May 12, 2016, the disclosure of which is incorporated herein by reference.

BACKGROUND

This disclosure relates generally to light modulation and in particular to a light modulator using total internal reflection at an interface with a tunable conductive layer.

Terahertz radiation generally refers to electromagnetic radiation (light) having a frequency in a range from about 0.1 terahertz (THz) to about 300 THz (wavelength in a range from about 3 mm to about 1 µm), including mid- to far-infrared light. Such radiation has potential application in a number of fields, including high-bandwidth communication and imaging (e.g., for medical diagnostics and other applications in biology).

However, optical components to modulate the phase and/or intensity of terahertz radiation are not well developed, particularly for broadband applications. Techniques used in other frequency ranges (e.g., optical frequencies) are generally not suitable for terahertz radiation. Thus, new structures and techniques are desired.

Various modulators for terahertz radiation have been proposed. For example, in regard to intensity modulation, electrically controllable metamaterial structures based on split ring resonators (SRRs) have been fabricated on gallium arsenide (GaAs) semiconductor substrates. (H.-T. Chen et al., "Active terahertz metamaterial devices," *Nature* vol. 444, no. 7119, pp. 597-600 (November 2006); H.-T. Chen et al., "Experimental demonstration of frequency-agile terahertz metamaterials," *Nat. Photonics vol.* 2, no. 5, pp. 295-298 (April 2008)). Such structures can modulate transmission of a terahertz pulse at a specific frequency. However, the frequency range is limited, and the transmission loss is generally high (e.g., 50% loss with the device in its off state). As another example, graphene sandwiched between a hexagonal grid and a pair of wire grids has been used to modulate the transmission for a resonance using a high voltage (e.g., 600 V). (S. H. Lee et al., "Switching terahertz waves with gate-controlled active graphene metamaterials," *Nat. Mater. vol.* 11, no. 11, pp. 936-941 (2012)). As yet another example, SRRs fabricated on a graphene layer have provided 18% modulation depth with lower gate voltages, but only at a specific frequency. (R. D. Innocenti et al., "Low-Bias Terahertz Amplitude Modulator Based on Split-Ring Resonators and Graphene," *ACS Nano* vol. 8, no. 3, pp. 2548-2554 (2014)). In another example, patterning a graphene layer with a set of ring apertures has been used to increase the modulation depth to around 50% over a small range of frequencies. (W. Gao et al, "High-contrast terahertz wave modulation by gated graphene enhanced by extraordinary transmission through ring apertures," *Nano Lett.* vol. 14, no. 3, pp. 1242-1248 (2014)). Still another example employs graphene deposited on top of a linear polarizer structure, providing 80% modulation depth over a larger frequency range with relatively low gate voltages. (S. F. Shi et al., "Optimizing Broadband Terahertz Modulation with Hybrid Graphene/Metasurface Structures," Nano Lett. vol. 15, pp. 372-377 (2015)). However, the grating parameters of the linear polarizer limit the frequency range, and performance rapidly falls off as frequency increases.

Examples of phase modulators include a modulator that uses the resonance of an electric SRR array and an external voltage to alter the phase of a terahertz pulse at a single frequency (just off the resonant peak of the SRR array). (H. Chen et al., "A metamaterial sold-state terahertz phase modulator," *Nat. Photonics* vol. 3, pp. 148-151 (2009)). Gate-controlled graphene metasurfaces provide a controllable phase modulation but with variable intensity in the on and off states. (Z. Miao et al., "Widely Tunable Terahertz Phase Modulation, with Gate-Controlled Graphene Materials," *Phys. Rev. X*, vol. 5 p. 014027 (2015)).

In all of the above examples, the frequency range is limited, in some cases to a very small range. This is in part due to the reliance on resonance phenomena. Some of the above examples also suffer from other drawbacks, such as high voltages and/or inefficient transmission of light when the modulator is in its off state.

Another approach uses total internal reflection (TIR) at a surface with a variable index of refraction to provide spatial modulation in the terahertz range. (M. Koch et al., "Modulator of electromagnetic waves," European Patent Publication 2 597 509 A1 (2013)). For example, a liquid crystal (LC) cell can be placed on the TIR surface of a prism, and the refractive index of the LC cell can be controlled (e.g., by applying a voltage to change the orientation of the LC molecules) to allow switching between TIR and non-TIR conditions. However, relatively thick LC cells would be required, and the voltage needed to switch such cells may be expected to result in slow and inefficient operation.

Accordingly, improved modulators for terahertz radiation would be desirable. Such modulators may provide, among other things, improved efficiency, broadband operating capability, good modulation depth, and/or other desirable features.

SUMMARY

The present invention relates to light modulators suitable for terahertz radiation. According to certain embodiments of the invention, a light modulator may be constructed using a prism in which light undergoes total internal reflection (TIR) at one surface. A tunable conductive layer is disposed on the TIR surface. The tunable conductive layer can be optically thin such that it does not affect the conditions under which TIR occurs. The tunable conductive layer can have a conductivity that is dynamically controllable by increasing or decreasing the availability of free carriers, for instance, by applying an electrical potential (voltage) across the tunable conductive layer or by optically pumping the tunable conductive layer. The tunable conductive layer can absorb a portion of the reflected light beam, attenuating the beam (also referred to as reducing the intensity of the beam). The amount of attenuation can be a function of the electrical conductivity of the tunable conductive layer. Accordingly, by controlling the conductivity of the tunable conductive layer, modulation of a light beam in the terahertz range can be achieved. In some embodiments, the tunable conductive layer can modify the phase of the reflected light beam in addition to (or instead of) the intensity, and various light modulators described herein can be constructed and operated to modulate intensity and/or phase as desired.

In some embodiments, the tunable conductive layer can have a spatial pattern applied to it, such that electrical conductivity is a function of position on a surface of the tunable conductive layer. When a light beam having finite width is incident on the spatial pattern, different portions of the light beam will experience different attenuations and/or phase shifts. In this manner, spatial light modulation can be provided. The spatial pattern can be time-varying.

In some embodiments, the tunable conductive layer can be made of a material having the property that attenuation is not strongly dependent on frequency (or wavelength) of the incident light, and such materials can be used to provide a broadband modulator. In other embodiments, the tunable conductive layer can have a conductivity that is a function of frequency, and such materials can be used to provide a bandpass filter (e.g., low-pass or high-pass filter).

In some embodiments, the tunable conductive layer can be made of a material such as graphene whose conductivity can be controlled by applying an electrical potential (voltage) across the material. For example, two (or more) electrodes can be disposed on opposite sides of a graphene layer. One electrode can be held at constant potential (e.g., 0 V) while the other provides a variable gate voltage (e.g., in a range from −9 V to +15 V or from −0.2 V to +2 V). The electrical potential can increase the availability of charge carriers and therefore the conductivity of the graphene layer.

In some embodiments, the tunable conductive layer can be made of a material such as graphene whose conductivity can be controlled using optical pumping. For example, a light source (including, e.g., an LED or laser or the like) can be arranged to direct pumping light from outside the prism onto the tunable conductive layer. This pumping light can be in a different frequency region from the light that is to be modulated; for instance, the modulated light can be terahertz radiation while the pumping light is in the visible frequency band. The frequency of the pumping light can be chosen to drive electrons of the tunable conductive layer into a higher energy state, thereby increasing conductivity.

Various materials can be used for the tunable conductive layer, including but not limited to graphene, silicon, vanadium dioxide, gallium arsenide, or other III-V semiconductors. The conductivity of the tunable conductive layer can be controlled electrically or optically. For spatial modulation, a pattern of conductivity across the surface of the tunable conductive layer can be created optically by applying different intensities of pumping light to different regions, or electrically by providing an array of separately controllable electrodes to create a pattern of different applied voltages at different locations of the tunable conductive layer.

In some embodiments, a metamaterial can be incorporated into the tunable conductive layer. Examples of suitable metamaterials include an array of split ring resonators (SRRs) or a metallic grating. Where used, the metamaterial can provide further shaping and control of the conductivity of the tunable conductive layer.

The following detailed description, together with the accompanying drawings, will provide a better understanding of the nature and advantages of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11A shows the evolution of the time domain waveform from the center of the device for various gate voltages. FIG. 11B shows the modulation depth at different gate voltages and frequencies of incident light. FIG. 11C shows the intensity for the transmitted (T), reflected s-polarization, and reflected p-polarization as a function of conductivity of the tunable conductive layer.

FIG. 13A shows the evolution of the time domain waveform from the center of the device for various gate voltages. FIG. 13B shows the modulation depth at different gate voltages and frequencies of incident light. FIG. 13C shows reflectance as a function of gate voltage.

FIG. 14A shows the evolution of the time domain waveform as the diode current is increased from 0 mA to 1500 mA in the example device. FIG. 14B shows the modulation depth as a function of frequency.

DETAILED DESCRIPTION

Embodiments of the invention described herein exploit the well-known phenomenon of total internal reflection (TIR), in which light (electromagnetic radiation) traveling through a medium with a first refractive index ($n_1$) is reflected at a surface that interfaces to another medium with a second refractive index ($n_2$) when the angle of incidence ($\theta_i$) satisfies the following condition:

$$\sin\theta_i > \frac{n_2}{n_1}. \quad (1)$$

This condition can occur for any combination of media where $n_1 > n_2$.

When a light beam of nonzero width undergoes TIR, a related phenomenon known as the Goos-Hänchen shift (G-H shift) occurs. According to this phenomenon, the reflected light travels a short distance along the interface before reflecting back. This distance depends on the wavelength (or frequency) of the light, as well as the refractive indexes of the two media and the angle of incidence.

The idea that the light travels along the interface between the two materials suggests that if the interface is conductive (i.e., if charge carriers can move freely on it), then the interaction length will be increased under TIR conditions relative to transmission (non-TIR) conditions. Using Maxwell's equations and the electromagnetic boundary conditions (including a surface charge), the following reflection coefficients can be derived for s- and p-polarization in the TIR condition:

$$r_S = \frac{n_1 \cos\theta_i - i\sqrt{n_1^2 \sin^2\theta_i - n_2^2} - Z_0 \sigma_S}{n_1 \cos\theta_i + i\sqrt{n_1^2 \sin^2\theta_i - n_2^2} + Z_0 \sigma_S}, \quad (2)$$

$$r_p = \frac{in_1\sqrt{n_1^2\sin^2\theta_i - n_2^2} - n_2^2\cos\theta_i - iZ_0\sigma_S\cos\theta_i\sqrt{n_1^2\sin^2\theta_i - n_2^2}}{in_1\sqrt{n_1^2\sin^2\theta_i - n_2^2} + n_2^2\cos\theta_i + iZ_0\sigma_S\cos\theta_i\sqrt{n_1^2\sin^2\theta_i - n_2^2}}, \quad (3)$$

where $Z_0$ is the vacuum impedance (377Ω) and $\sigma_s$ is the conductivity at the boundary (assumed for present purposes to be a discrete sheet or layer of material; examples are described below). These equations predict 100% reflection in the case where the sheet has zero conductivity and 0% in the case where the numerators go to zero. The functions are continuous, and any amount of reflection (from 0 to 100%) is theoretically possible. In applications where the two media and angle of incidence are held constant, the reflection coefficients can be controlled by controlling the sheet conductivity $\sigma_s$.

Accordingly, light modulators according to embodiments of the present invention can be constructed by providing a thin layer or sheet having controllable conductivity at an interface where TIR occurs.

Figure 1:
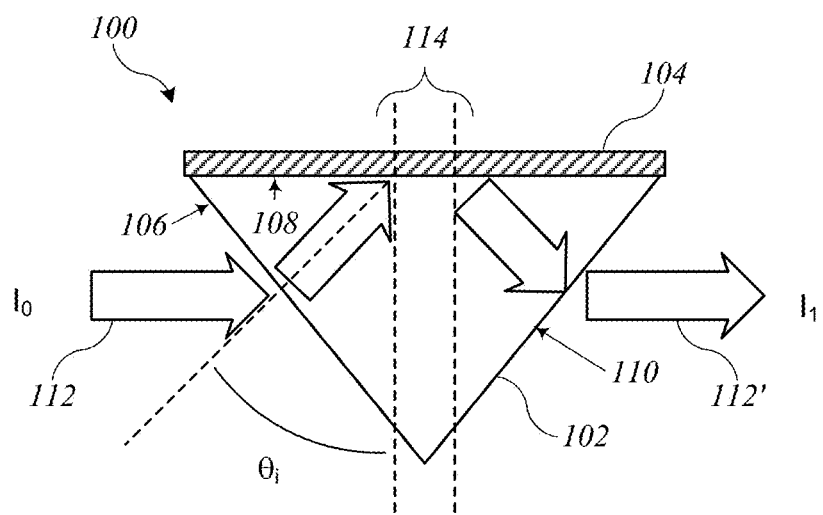
FIG. 1 shows a simplified schematic side view of a light modulator according to an embodiment of the present invention.

FIG. 1 shows a simplified side view of a modulator 100 according to an embodiment of the present invention. Modulator 100 includes a prism 102 and a tunable conductive layer 104 disposed on a surface of prism 102. (Unless otherwise indicated, drawings are not to scale.)

Prism 102 can be made of any material that is optically transparent to electromagnetic radiation (also referred to herein as "light," which is to be understood as not limited to visible light) in a frequency range of interest and that has a higher refractive index than a surrounding medium (e.g., air, for which refractive index n is approximately 1.0). For example, the frequency range of interest may correspond to terahertz radiation (frequency about 0.1 THz to about 300 THz or, equivalently, wavelengths from about 3 mm to about 1 µm). Suitable materials for prism 102 in that case include quartz (refractive index n approximately 2.12), sapphire (n approximately 3), silicon (n approximately 3.42), optically transparent polymers such as cyclic olefin copolymer (n approximately 1.56) available from TOPAS Advanced Polymers GmbH of Frankfurt, Germany (referred to as "TOPAS polymers"), and any other optically transparent material with a refractive index greater than that of the surrounding medium in which prism 100 is to be used.

Prism 102 has an entrance surface 106, a TIR surface 108, and an exit surface 110. An input light beam (indicated by arrows) 112, having an initial intensity $I_0$ is refracted by entrance surface 106 and strikes TIR surface 108 at an angle $\theta_i$ that is at least equal to the critical angle $\theta_c$, which is the angle that satisfies $\sin\theta_c = n_2/n_1$. Total internal refection occurs, together with a G-H shift (as indicated schematically by vertical lines 114), and an output light beam 112' exits prism 102 at exit surface 110, with an intensity $I_1$ that may be less than or equal to $I_0$.

Tunable conductive layer 104 is disposed on TIR surface 108 of prism 102. Tunable conductive layer 104 can be an optically thin layer (thin enough that it does not affect the conditions for TIR, such as the critical angle) and can be made of any substance whose conductivity ($\sigma_s$) can be controllably varied during device operation (referred to as being "tunable"). For example, tunable conductive layer 104 can be made of graphene, silicon, vanadium dioxide, gallium arsenide, other III-V semiconductors, or other materials whose conductivity can be controllably varied using optical and/or electronic techniques. Specific examples are described below.

Figure 2:
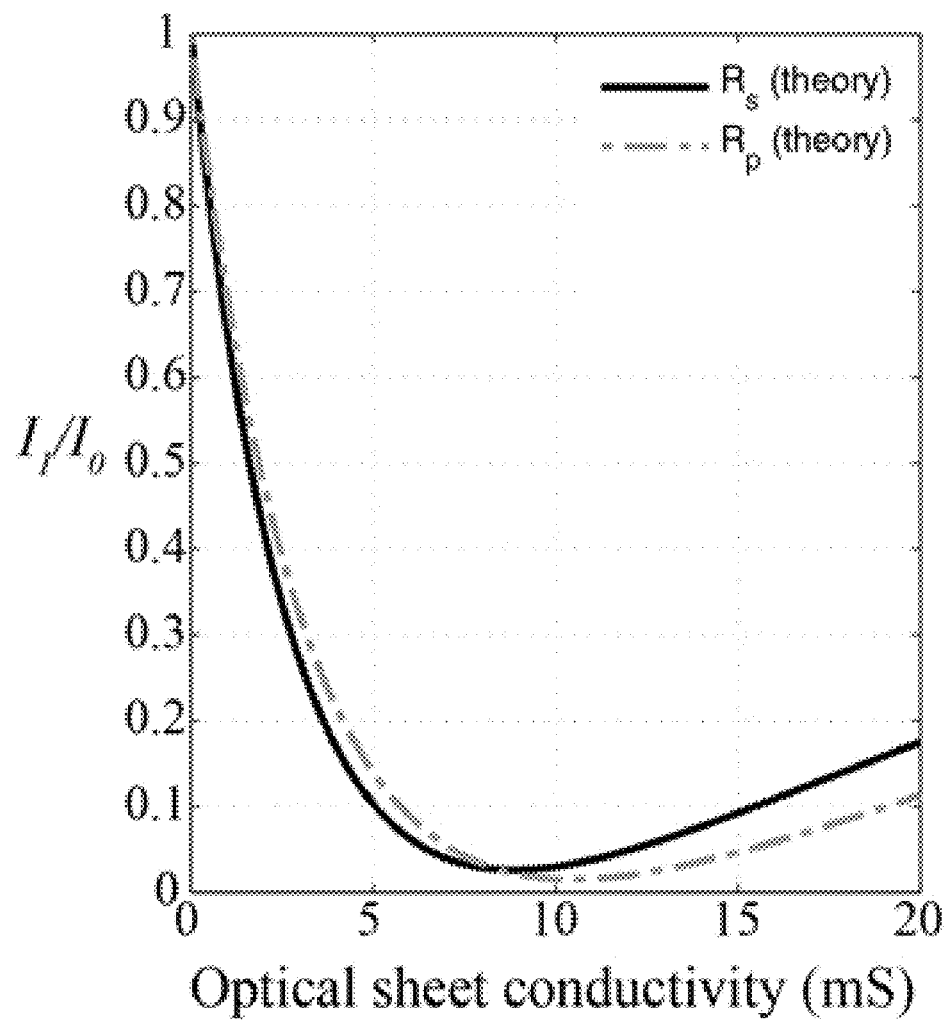
FIG. 2 shows a graph illustrating an intensity modulation effect for an interface between a prism and a surrounding medium according to an embodiment of the present invention.

In operation, tunable conductive layer 104 can change the intensity and/or phase of output light beam 112' relative to input light beam 112. The particular change can be a function of the conductivity $\sigma_s$ of tunable conductive layer 104 (see, e.g., Equations (2) and (3) above). Accordingly, by varying the conductivity of tunable conductive layer 104, it is possible to modulate the intensity of light beam 112'. FIG. 2 shows a graph illustrating an intensity modulation effect for an interface between prism 102 and a surrounding medium according to an embodiment of the present invention. For purposes of this graph, it is assumed that the prism has $n_1 = 3.42$) and the surrounding medium has $n_2 = 1.00$. The angle of incidence $\theta_i$ is assumed to be 24.6° (above the critical angle). Plotted in FIG. 2 is the relative intensity ($I_1/I_0$) of the output light beam as a function of conductivity $\sigma_s$ of tunable conductive layer 104 (in millisiemens (mS)), for s-polarized and p-polarized light. In this example, intensity is at a maximum when the conductivity is zero and at a minimum for conductivity between about 8 and 10 mS (the minimum is slightly different for s- and p-polarized light).

Figure 3:
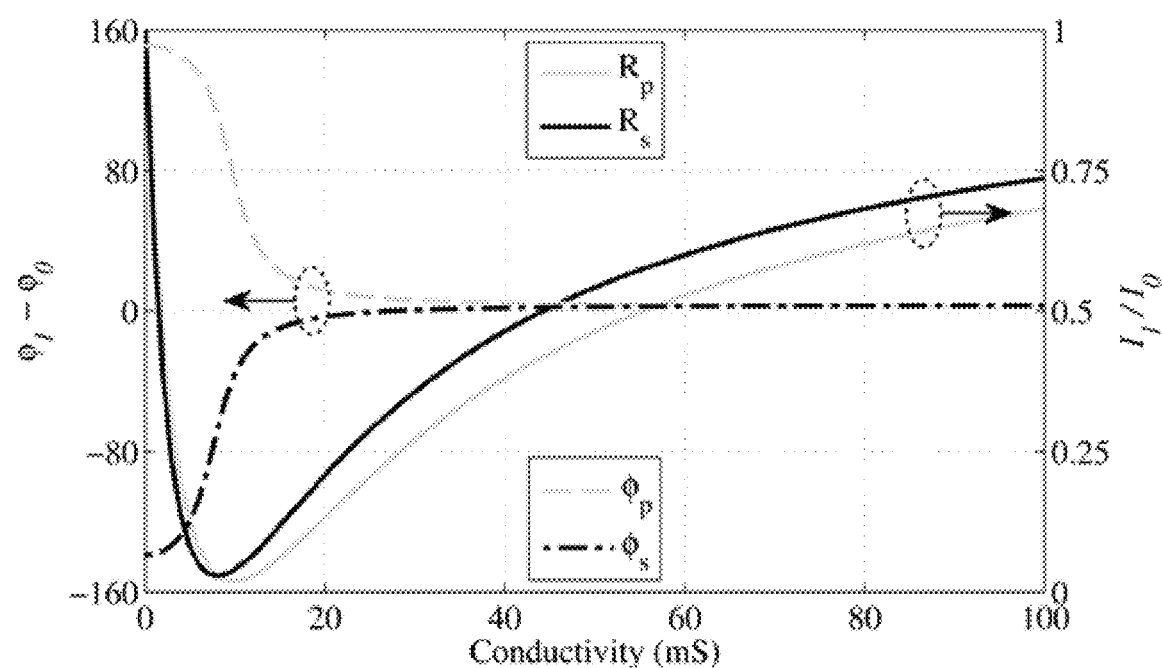
FIG. 3 shows a graph illustrating a phase modulation effect for an interface between a prism and a surrounding medium according to an embodiment of the present invention.

In some embodiments, the phase angle of output light beam 112' relative to input light beam 112 can also be modulated using tunable conductive layer 104. As with reflectance, the phase angle change is a function of conductivity $\sigma_s$ of tunable conductive layer 104. FIG. 3 shows a graph illustrating a phase modulation effect for an interface between prism 102 and a surrounding medium according to an embodiment of the present invention. For purposes of this graph, it is assumed that the prism has $n_1 = 3$ and the surrounding medium has $n_2 = 1$. The angle of incidence $\theta_i$ is assumed to be 26.2° (above the critical angle), and incident light beam 112 is assumed to have a frequency of 0.5 THz. The difference in phase angle ($\phi_1 - \phi_0$) between the output light beam and the input light beam, as a function of conductivity $\sigma_s$ of tunable conductive layer 104, is shown, using broken lines, for both s- and p-polarized light, referencing the left axis. As can be seen, large phase shifts can be created to the extent that the incident beam is polarized. Also shown, using solid lines and referencing the right axis, is the relative intensity ($I_1/I_0$) of the exiting light as a function of conductivity $\sigma_s$ of tunable conductive layer 104, similar to FIG. 2. Both intensity modulation and phase modulation can occur at the same time, and both are functions of conductivity $\sigma_s$.

FIG. 3 shows that phase modulation depends on conductivity and that the phase modulation effect is different for s-polarized and p-polarized light. For example, at conductivity of 4 mS, the phase difference between s- and p-polarized light is 273.6°, while at 60 mS, the phase difference is zero. It is therefore possible to provide a controllable quarter waveplate. Other types of waveplates (e.g., half waveplate) can also be provided as a function of the conductivity.

It will be appreciated that modulator 100 is illustrative and that variations and modifications are possible. Prism 102 can be made of any material or combination of materials that provides total internal reflection from at least one surface. The shape of prism 102 can also be varied. Examples shown herein use triangular prisms, but other shapes such as a Dove prism or Fresnel rhomb can be substituted. Some prisms can provide multiple TIR surfaces, and a tunable conductive layer can be disposed on one or more of the TIR surfaces as desired.

Figure 4:
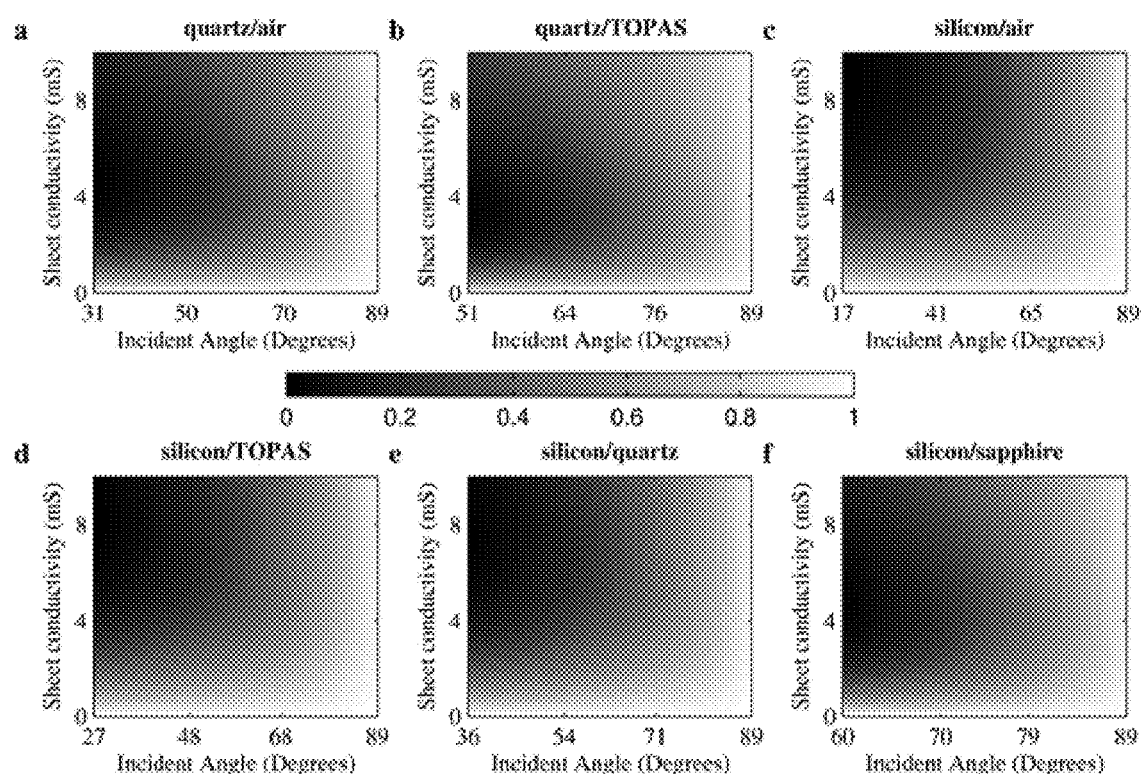
FIG. 4 shows six graphs illustrating reflectance as a function of angle of incidence and conductivity of a tunable conductive layer for a variety of interfaces between different prism and environment materials that may be used according to various embodiments of the present invention.

It should also be understood that no particular angle of incidence at TIR surface 108 is required, provided that the angle of incidence is equal to or greater than the critical angle. FIG. 4 shows six graphs illustrating the reflectance (gray scale, with lighter shades corresponding to higher reflectance) as a function of angle of incidence (horizontal axis) and conductivity of tunable conductive layer 104 for a variety of interfaces between different materials (prism/environment). Shown are graphs for: (a) quartz/air; (b) quartz/TOPAS polymer; (c) silicon/air; (d) silicon/TOPAS polymer; (e) silicon/quartz; and (f) silicon/sapphire. As can be seen, a dependence of reflectance on conductivity is present across a range of angles of incidence, becoming weaker at the very highest angles.

In the embodiments described herein, tunable conductive layer 104 has a conductivity that is controllably variable. Accordingly, some embodiments of the present invention incorporate control mechanisms to provide control over the conductivity of tunable conductive layer 104. In some applications, varying the conductivity dynamically (as a function of time) can allow for signal communication. For instance, the varying intensity and/or phase of the output beam can communicate information, such as binary data, using signaling schemes known in the art. In some embodiments, the control mechanism may also allow the conductivity to be varied spatially, so that at a given time, different regions within tunable conductive layer 104 have different conductivity. Such spatial control mechanisms can support spatial light modulation (SLM), which can increase the density of information in the signal. (For instance, conventional signal processing algorithms can be used to reconstruct an image including a pattern of light and dark areas using a single source and a single detector; this pattern can convey multiple bits of binary data or other information.) It is to be understood, however, that the present invention is not limited to signaling applications and that embodiments of the invention may be used in any context in which light modulation is desired.

Examples of control mechanisms that can be used to control the conductivity of tunable conductive layer 104 will now be described.

Figure 5:
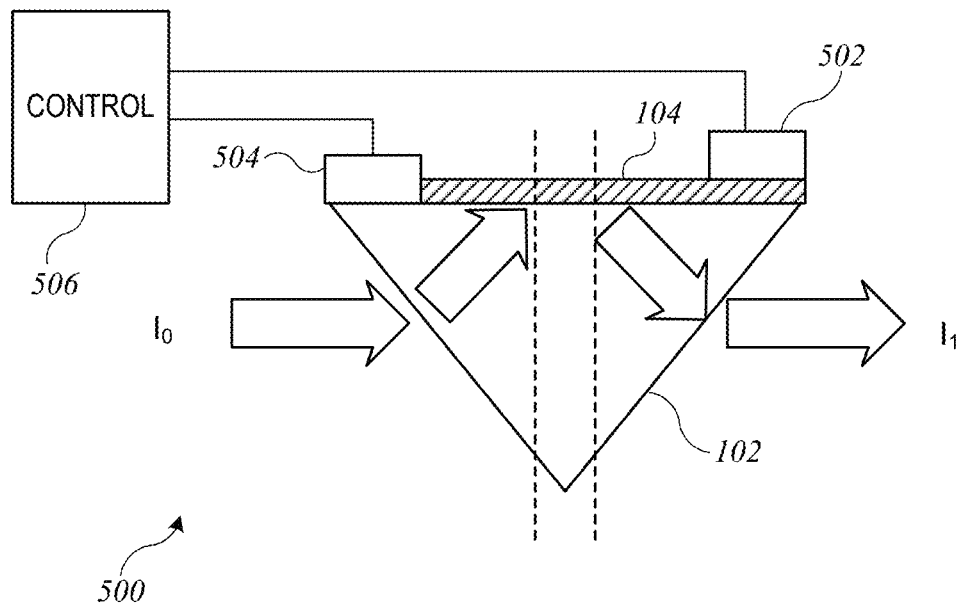
FIG. 5 shows a simplified schematic side view of a modulator system that includes an electrical control mechanism according to an embodiment of the present invention.

One type of control mechanism is electrical. FIG. 5 shows a simplified schematic side view of a modulator system 500 that includes an electrical control mechanism according to an embodiment of the present invention. Modulator system 500 can include prism 102 and tunable conductive layer 104 as described above. In this example electrodes 502 and 504 are disposed to make electrical contact with tunable conductive layer 104 at different points. For example, electrode 502 may contact a point near or at a top surface of tunable conductive layer 104 while electrode 504 contacts a point at or near a bottom surface of tunable conductive layer 104.

Electrodes 502 and 504 can be electrically connected to a control unit 506. Control unit 506 can include driver circuitry (not explicitly shown) to generate a voltage difference between electrodes 502 and 504. Such driver circuitry can be of conventional design, and a detailed description is omitted. In some embodiments, control of the voltage generated by the driver circuitry can be achieved through a manual interface to control unit 506. For instance, control unit 506 can include a dial or input buttons or the like (not explicitly shown) via which a user can provide input. In some embodiments, the user input can specify a desired voltage. In other embodiments, the user input can specify a desired conductivity for tunable conductive layer 104 (or a desired effect on the intensity and/or phase of the light beam), and control unit 506 can include programmed or dedicated logic circuits to determine the corresponding voltage (e.g., by accessing a lookup table). In other embodiments, control can be automated using a microcontroller that is programmed to determine the voltage corresponding to a desired modulation effect and generate appropriate control signals to the driver circuitry. The particular programming may depend on a specific application (e.g., a particular signaling protocol) in which modulator 500 is being used; those skilled in the art with access to the present disclosure will be able to develop suitable programming for specific applications. It is to be understood that this programming can provide for time domain modulation, such that the conductivity of tunable conductive layer 104 (and therefore the intensity and/or phase of the output light beam) varies with time. Details of the control logic and interfaces are not believed to be critical to understanding the claimed invention.

Figure 6:
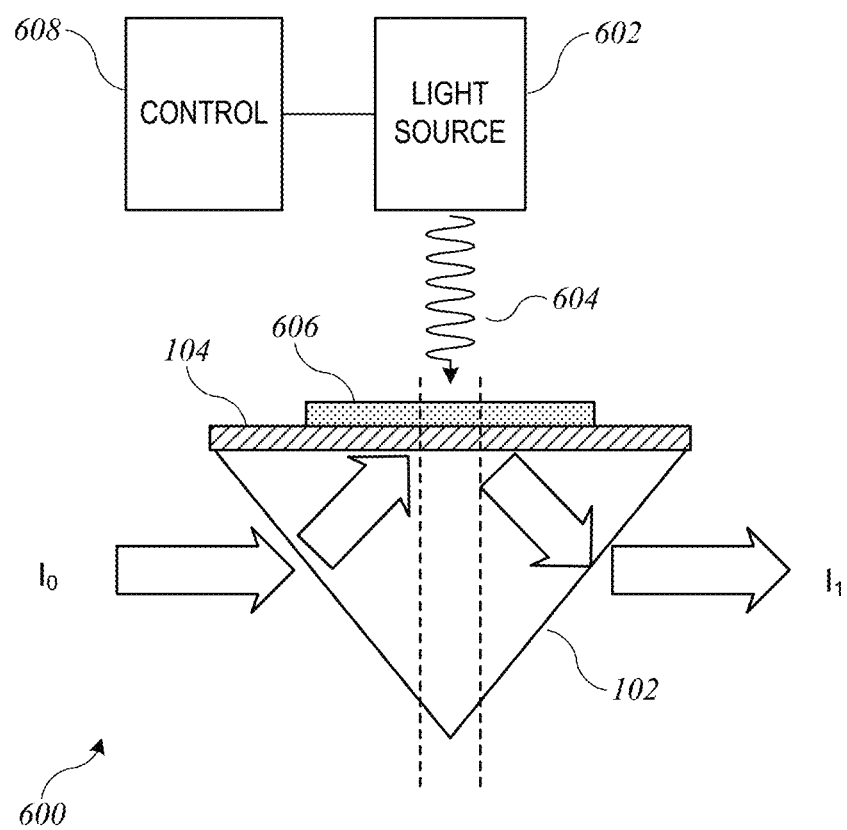
FIG. 6 shows a simplified schematic side view of a modulator system that includes an optical control mechanism according to an embodiment of the present invention.

Another type of control mechanism is optical. FIG. 6 shows a simplified schematic side view of a modulator system 600 that includes an optical control mechanism according to an embodiment of the present invention. Modulator system 600 can include prism 102 and tunable conductive layer 104 as described above. A light source 602 can generate a pumping light beam 604 and direct pumping light beam 604 toward tunable conductive layer 104. An antireflective coating 606 can be applied to the top surface of tunable conductive layer 104 to improve coupling of pumping light beam 604 into tunable conductive layer 104. Antireflective coating 606 can be made of suitable materials (e.g., materials with refractive index intermediate between tunable conductive layer 104 and the surrounding medium).

In this example, light source 602 can incorporate a laser or LED or the like to generate light in a narrow frequency band. The frequency band can be chosen to provide optical pumping of tunable conductive layer 104, which can be, e.g., a semiconductor material. Optical pumping can drive electrons in tunable conductive layer 104 into a higher energy state, thereby increasing the conductivity of tunable conductive layer 104. The particular choice of optical pumping frequency depends on the material properties of tunable conductive layer 104. Those skilled in the art with access to the present disclosure will be easily able to determine appropriate frequencies for a given material. When optical pumping is discontinued (or reduced in intensity), the conductivity of tunable conductive layer 104 may also be reduced. Accordingly, optical control of the conductivity of tunable conductive layer 104 can be provided.

Light source 602 can be connected to a control unit 608. Control unit 608 can include appropriate circuitry to generate a control signal or driving current for light source 602 to produce pumping light beam 604 at a desired intensity, based on the desired conductivity of tunable conductive layer 104. The desired conductivity can be provided by user input and/or programming, similarly to embodiments of control unit 506 described above. (Again, details of the control logic and interfaces are not believed to be critical to understanding the claimed invention.)

Figure 7:
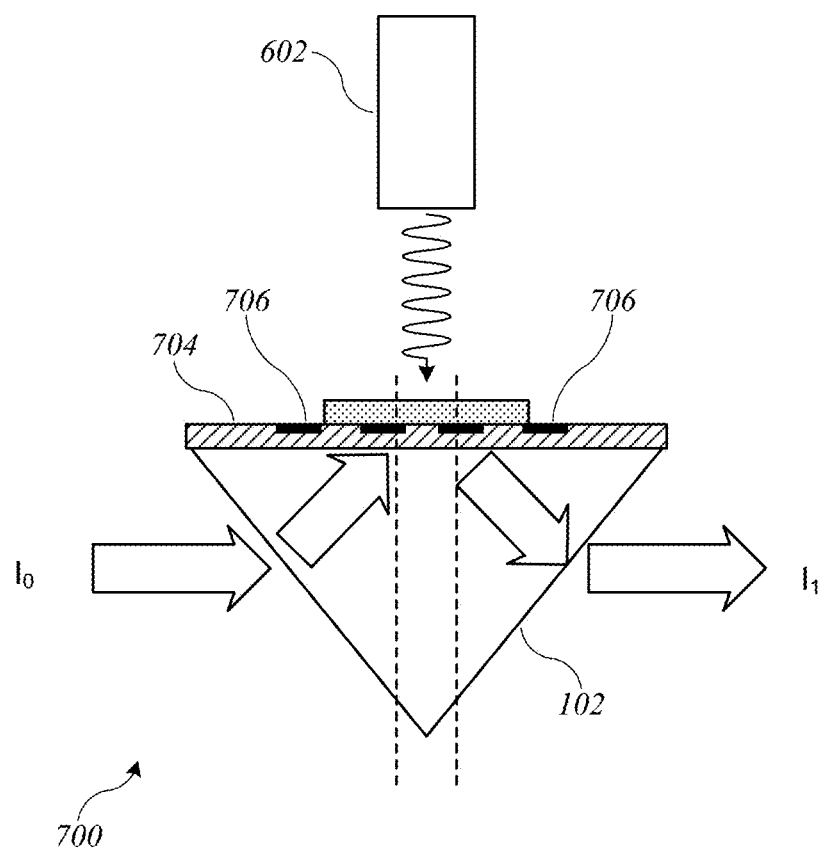
FIG. 7 shows a simplified schematic perspective view of a modulator system that includes a metamaterial according to an embodiment of the present invention.

In some embodiments, a metamaterial can be incorporated into tunable conductive layer 104 to further shape the conductivity and consequently, the attenuation and/or phase shift of the incident light. FIG. 7 shows a simplified schematic side view of a modulator system 700 incorporating a metamaterial according to an embodiment of the present invention. Modulator system 700 can be similar to modulator system 600 of FIG. 6, including light source 602 and control unit 608 (not shown in FIG. 7). The modulator can include prism 102 and tunable conductive layer 704. Tunable conductive layer 704 can be similar to tunable conductive layer 104 except that tunable conductive layer 704 includes metamaterial structures 706. As used herein, a "metamaterial structure" refers generally to a material that has been engineered (e.g., at the nanoscale) to have desired electrical and/or optical properties. Examples include metal gratings, resonators (e.g., split ring resonators (SRRs)), ring apertures, and so on, which can be fabricated using techniques known in the art. The inclusion of metamaterials is optional, and a particular choice of metamaterial will be application-dependent.

Figure 8:
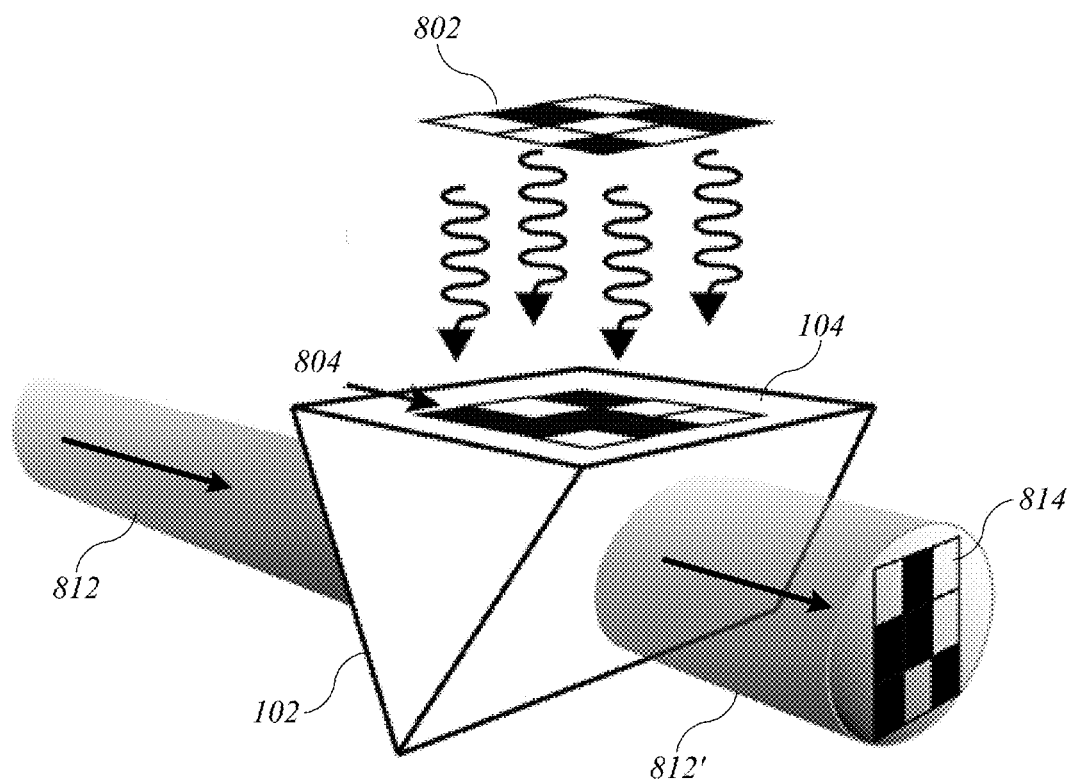
FIG. 8 shows a simplified schematic side view of a spatial light modulator system according to an embodiment of the present invention.

The modulator systems shown in FIGS. 5-7 can provide light modulation in the time domain by varying the conductivity of tunable conductive layer 104 (or 704) as a function of time. In some embodiments, it may also be desirable to provide spatial light modulation (SLM). FIG. 8 shows a simplified schematic perspective view of a spatial light modulator system 800 according to an embodiment of the present invention. Modulator system 800 can be similar to modulator system 600 of FIG. 6, including prism 102 and tunable conductive layer 104. In this example, light source 802 is an LCD visible-frequency spatial light modulator, which can be of generally conventional design. Light source 802 can generate a two-dimensional pattern of light and dark areas and can direct this illumination pattern onto tunable conductive layer 104. This pattern can provide different amounts of optical pumping to different areas on tunable conductive layer 104, as indicated by pattern 804. As a result, portions of input light beam 812 that strike different portions of the TIR interface between prism 102 and tunable conductive layer 104 experience different attenuations, resulting in an output light beam 812' having a spatially modulated intensity, as indicated by pattern 814. It is to be understood that the pattern generated by light source 802 can be time varying. A control unit similar to control unit 608 of FIG. 6 can be coupled to the light source to facilitate control of the spatial pattern (or a sequence of spatial patterns) generated by light source 802.

While FIG. 8 shows SLM using an optical control mechanism, those skilled in the art with access to the present disclosure will appreciate that an electrical control mechanism can also provide SLM capability. For example, an array of independently controllable electrodes can be electrically connected to different portions of tunable conductive layer 104, thereby allowing the conductivity to be varied as a function of position as well as time.

In some embodiments, modulator 100 can be used to provide bandpass filtering. For example, tunable conductive layer 104 (or 704) can be designed to provide a conductive response that is strongly frequency dependent. This can be accomplished through the choice of materials and/or metamaterials to include in tunable conductive layer 104 (or 704).

Figure 9:
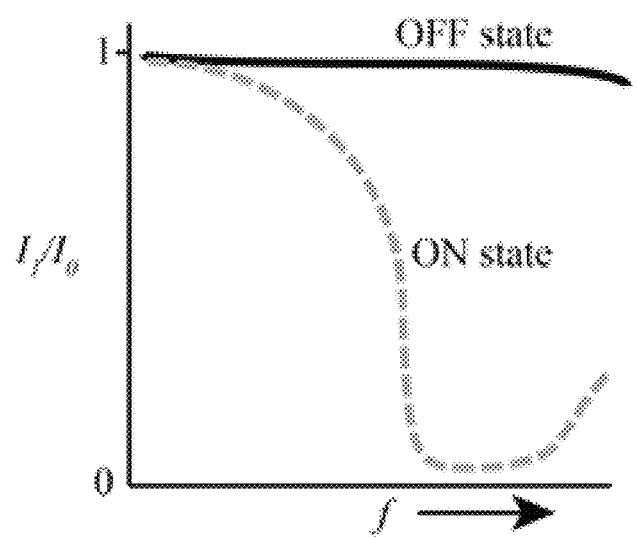
FIG. 9 shows a graph of a low-pass filter implementation according to an embodiment of the present invention.

FIG. 9 shows a graph of a low-pass filter implementation according to an embodiment of the present invention. In this example, when tunable conductive layer 104 (or 704) is in an "off" state (e.g., conductivity is at a minimum), the frequency response is approximately uniform. When tunable conductive layer 104 (or 704) is switched to an "on" state (conductivity greater than the minimum), e.g., via optical pumping or electrical potential as described above, the response can be significantly dependent on frequency (f). As shown in FIG. 9, frequencies below a cutoff may have little attenuation while above the cutoff, attenuation increases sharply. High-pass filters can be implemented similarly, with a different combination of materials and/or metamaterials.

In some embodiments, modulator 100 can provide phase modulation in addition to or instead of intensity modulation. Like intensity modulation, phase modulation is a function of conductivity of tunable conductive layer 104 (e.g., as shown in FIG. 3). Accordingly, any of the modulator systems of FIGS. 5-8 can be used for phase modulation (including spatial modulation) in addition to or instead of intensity modulation.

The range of conductivity values over which phase modulation is of interest may be different from (e.g., larger than) the range of interest for intensity modulation. For instance, as shown in FIG. 3, intensity modulation reaches a minimum at a conductivity of about 8-10 mS. Phase modulation effects approach zero (no phase change) at a higher conductivity of about 25-30 mS. Accordingly, the choice of materials for tunable conductive layer 104 may depend on whether a particular modulator is intended for phase modulation or intensity modulation, as that may determine the range of conductivities that are of interest. In applications where relatively low conductivities (e.g., below about 10 mS) are desired, graphene and III-V semiconductors may be preferred choices for tunable conductive layer 104. Such materials can provide intensity modulation with a modulation depth approaching 100% over the range of conductivity from 0 to about 10 mS, with the exact parameters depending on the material. In applications where a larger range of conductivities is desired (as may be the case for phase modulation), tunable conductive layer 104 may preferably be made of a material such as vanadium oxide that undergoes a material phase transformation from a low-conducting to a high-conducting material under the influence of electrical, optical, or temperature changes. Regardless of which material is used, metamaterial structures can be used to shape both the conductivity response of the tunable conductive layer and the resulting G-H shift (and consequently the properties of the output light beam).

Specific examples of light modulators according to embodiments of the present invention will now be described. It is to be understood that these examples are illustrative and not limiting.

Example 1

Figure 10A:
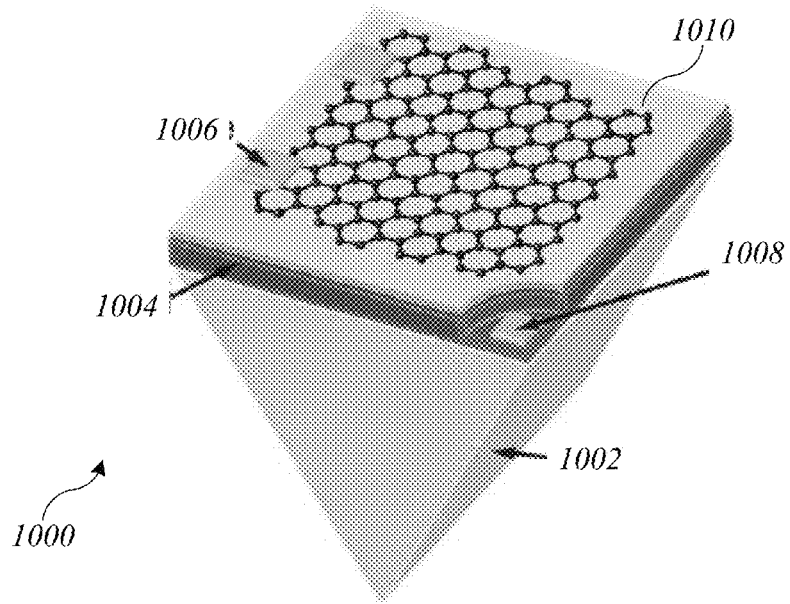
FIGS. 10A and 10B show, in simplified schematic and photographic views, respectively, a first light modulator constructed according to an embodiment of the present invention.

As shown in FIG. 10A (simplified schematic view) and 10B (photograph with annotations), a light modulator 1000 is constructed using a quartz prism 1002. The top (TIR) surface of prism 1002 can have an area of approximately 1 cm×1 cm. A substrate 1004 is formed of silicon (Si) and silicon dioxide ($SiO_2$). For example, substrate 1004 can include a 90-nm $SiO_2$ layer grown on lightly doped (e.g., ~100 Ωcm) Si using plasma enhanced chemical vapor deposition (PECVD). Electrodes 1006, 1008 can be made of gold or other suitable metal and deposited on the $SiO_2$ layer by thermal evaporation. Graphene layer 1010 (which can be a monolayer) can be transferred to the top of substrate 1004.

In operation, one of the electrodes (e.g., contact electrode 1006) can be held at a constant potential (e.g., 0 V) while a variable potential is applied to the other electrode (e.g., gate electrode 1008). The variable potential can be constrained to prevent electrical breakdown of the $SiO_2$ insulation layer. For example, the potential can be in a range from −9 V to +15 V.

Figure 10B:
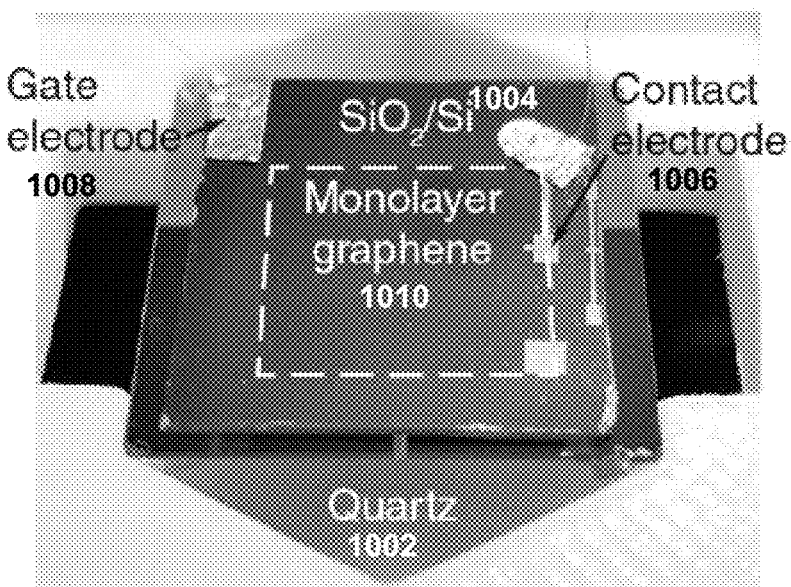
Figure 11A:
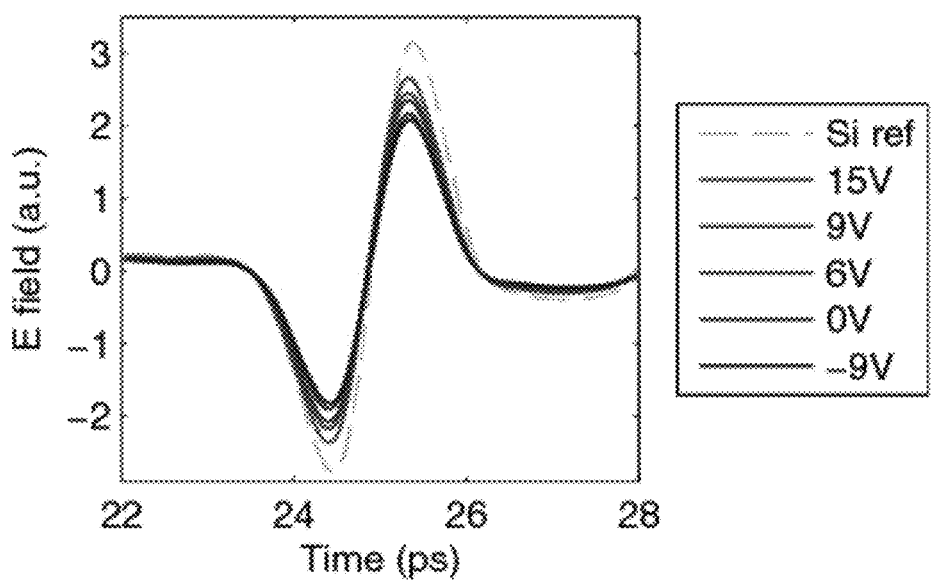
FIGS. 11A-11C show graphs of experimental results obtained for the device of FIGS. 10A and 10B.

FIG. 11A shows the evolution of the time domain waveform from the center of the graphene device as the voltage is swept from −9 V to +15 V in the device of FIG. 10B. The "Si ref" line represents the waveform with a bare Si wafer on the TIR surface in the absence of graphene. The time position does not shift, but the peak-to-peak value decreases by about 22% across this range.

Figure 11B:
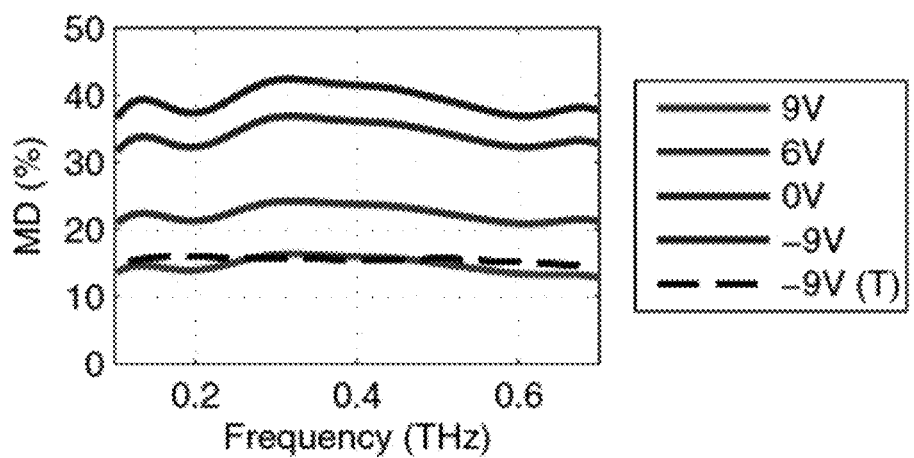

FIG. 11B shows the modulation depth at different gate voltages for the reflected beam at a range of frequencies from 0.1 to 0.7 THz, as measured for the device of FIG. 10B. Modulation depth (MD) is defined for this purpose as $$MD(V) = \left(1 - \frac{R(V)}{R_B}\right) \times 100\%, \quad (4)$$

where reflectance R(V) is defined as:

$$R(V) = \left(\frac{r(V)}{r_{Bare}}\right)^2. \quad (5)$$

In Equations (4) and (5), r(V) is the measured amplitude of the reflected electric field at the gate voltage V (e.g., as shown in FIG. 11A); $r_{Bare}$ is the measured amplitude of the reflected electric field for the reference configuration (bare Si wafer); and $R_B$ is a baseline reflectance, measured at the gate voltage corresponding to the charge neutrality point (CNP), which is where the conductivity of graphene is at its lowest. (In this case, the CNP corresponds to gate voltage of 15 V). The dashed line shows the maximum modulation depth in transmission (T) mode; the definition is similar to Equations (4) and (5), except that in transmission mode the angle of incidence is less than the critical angle (so that TIR does not occur), and the transmitted electric field, rather than a reflected electric field, is measured.

Figure 11C:
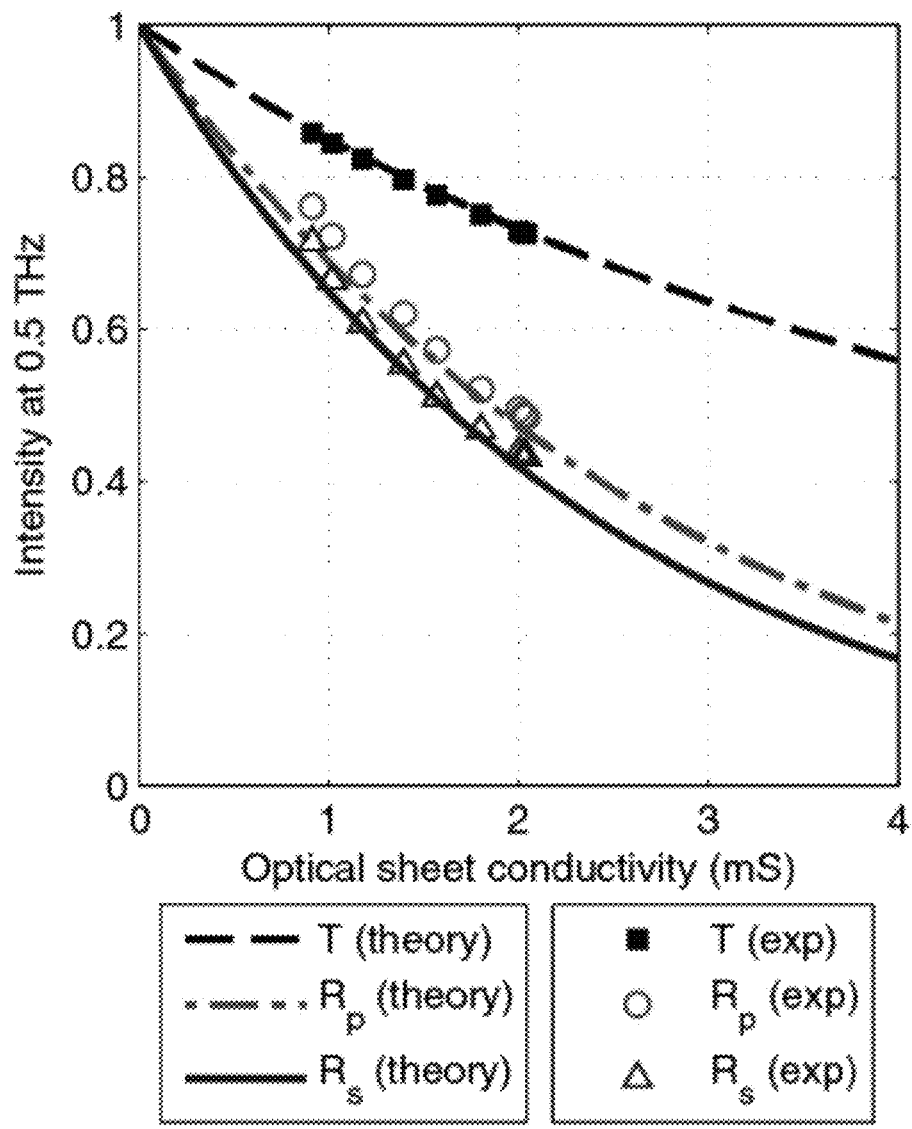

FIG. 11C shows the intensity for the transmitted (T), reflected s-polarization, and reflected p-polarization as a function of optical sheet conductivity for the device of FIG. 10B. Measurements (squares, circles, and triangles respectively) show good agreement with theoretical predictions (lines). Both theory and experiment show a higher modulation depth for s-polarization than p-polarization for a given change in conductivity. (Accordingly, the graphs in other figures are for s-polarization only, although it is to be understood that p-polarization may also be used.) It is also observed that the reflection mode provides greater modulation depth than the transmission mode; hence, the reflection mode is preferred as a modulator.

Example 2

Figure 12A:
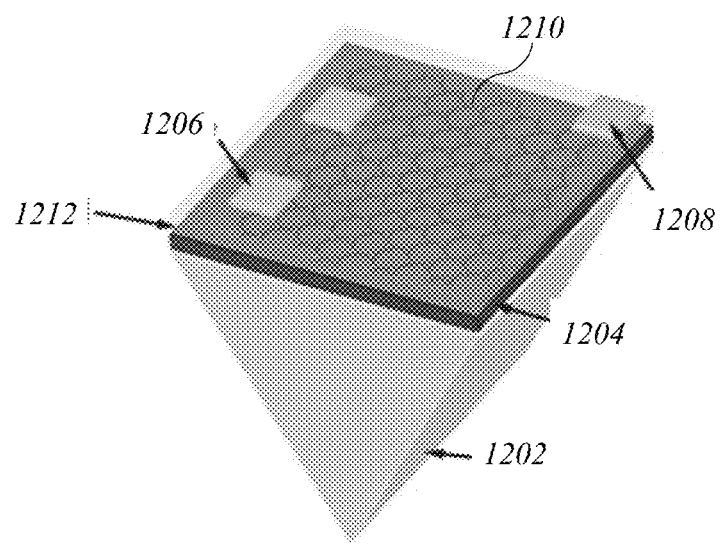
FIGS. 12A and 12B show, in simplified schematic and photographic views, respectively, a second light modulator constructed according to an embodiment of the present invention.

As shown in FIG. 12A (simplified schematic view) and 12B (photograph with annotations), a light modulator 1200 is constructed similarly to light modulator 1000 of FIGS. 10 and 10B. In particular, quartz prism 1202, substrate 1204, electrodes 1206, 1208, and graphene monolayer 1210 can be similar to quartz prism 1002, substrate 1004, electrodes 1006, 1008, and graphene monolayer 1010. In this example, the SiO2 layer of substrate 1004 has a thickness of around 200 nm.

In this example, light modulator 1200 also includes an ion-gel layer 1212 to support higher conductivity. For example, an ion-gel can be fabricated by mixing [EMIM][TFSI] ionic liquid, poly(ethylene glycol) diacrylate (PEGDA), and 2-hydroxy-2-methylpropiophenone (HOMPP) (UV cross-linking initiator) with a ratio of 88:8:4 (w/w). This ion-gel solution can be drop-cast on the top of graphene monolayer 1210 (e.g., prior to transferring graphene monolayer 1210 to substrate 1204) to form ion-gel layer 1212. UV exposure can be used to cure the ion-gel. Gate electrode 1208 is formed on top of ion-gel layer 1212.

In operation, one of the electrodes (e.g., contact electrode 1206) can be held at a constant potential (e.g., 0 V) while a variable potential is applied to the other electrode (e.g., gate electrode 1208). For example, the potential can be in a range from −0.2 V to +2 V. (As will be seen, a smaller range of potentials results in a larger variation in conductivity relative to Example 1.)

Figure 12B:
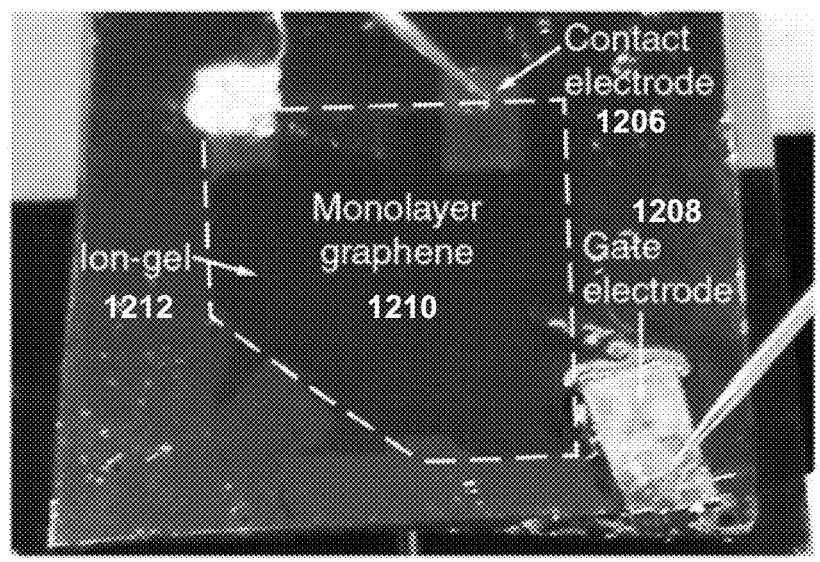
Figure 13A:
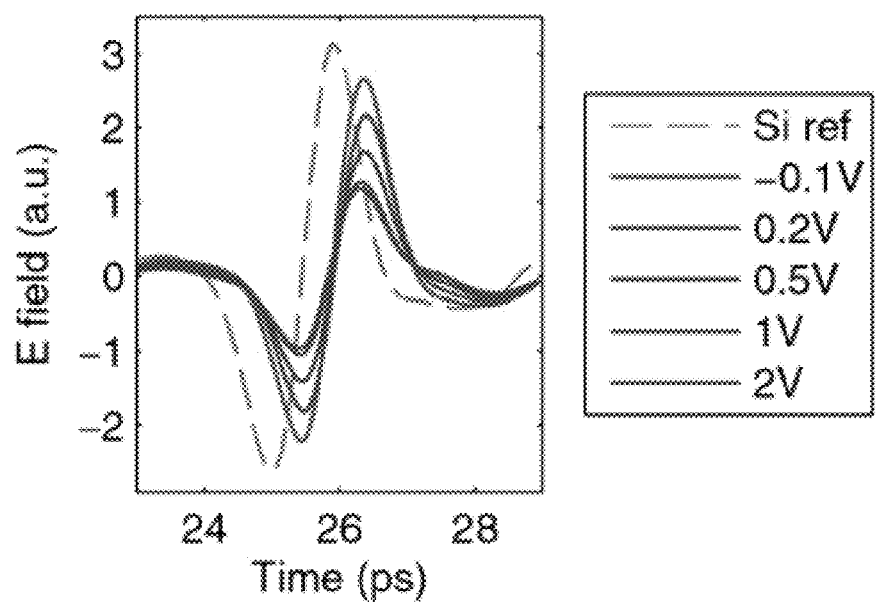
FIGS. 13A-13C show graphs of experimental results obtained for the device of FIGS. 12A and 12B.

FIG. 13A shows the evolution of the time domain waveform from the center of the graphene device as the voltage is swept from −0.2 V to +2 V in the device of FIG. 12B. Unlike the previous example, the time position does shift relative to the bare Si reference. This may be due to ion-gel layer 1212 altering the effective refractive index of the medium outside the TIR surface of prism 1202, which would be expected to increase phase delay of evanescent waves. However, ion-gel layer 1212 in this example is transparent to terahertz radiation, and the modulation effect can be attributed to the graphene. The modulation effect is seen as a 56% decrease in peak-to-peak value, a significantly greater effect than in FIG. 11A. This can be attributed to the high specific capacitance of the ion-gel gate (which is on the order of 10 μF/cm, much higher than the $SiO_2$ gate).

Figure 13B:
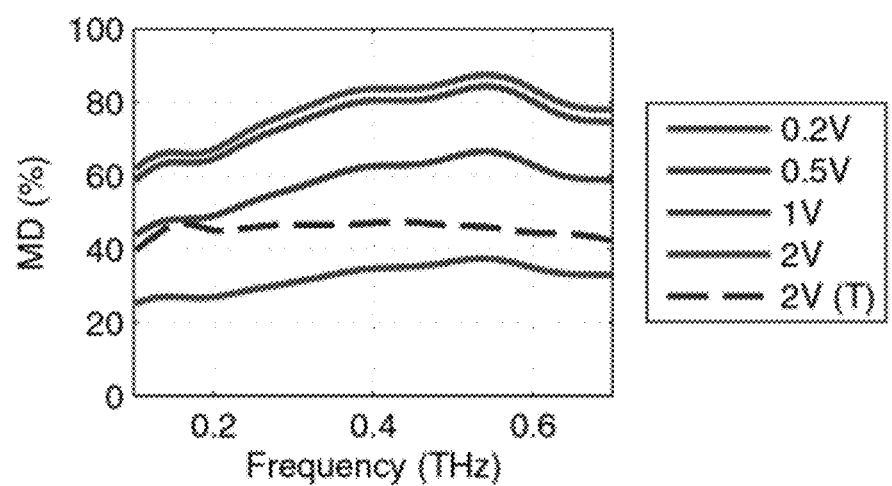

FIG. 13B shows the modulation depth at different gate voltages for the reflected beam at a range of frequencies from 0.1 to 0.7 THz, as measured for the device of FIG. 12B. The dashed line shows the modulation depth in transmission (T) mode. Modulation depth is defined as described above for FIG. 11B. As can be seen by comparing FIG. 13B and FIG. 11B, modulation depth is significantly increased with ion-gel layer 1212. Further, the modulation depth in the reflection (TIR) mode is much greater than the peak modulation depth in the transmission mode.

Figure 13C:
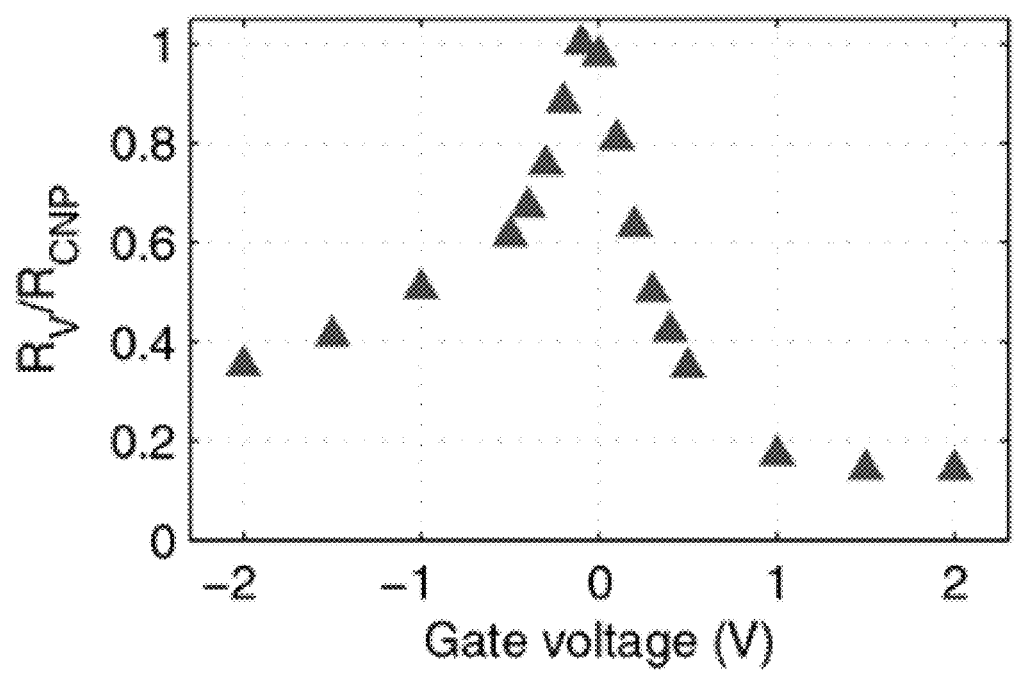

FIG. 13C shows reflectance as a function of gate voltage, normalized to the peak reflectance (which corresponds to the CNP, in this case a gate voltage of approximately −0.1 V), for the device of FIG. 12B. The reflected intensity becomes saturated at around 1.5 V to 2 V (and similarly for negative gate voltages). This may be attributed to the fact that the scattering effect of carriers increases as the concentration of carriers increases, which prevents conductivity from increasing linearly with concentration of carriers. The ambipolar behavior can be understood physically as well: above or below the CNP, the Fermi level is either above or below the CNP, and a departure in either direction enables charge transport, increasing conductivity. Performance is asymmetric, however, with greater modulation depth occurring at positive gate voltages.

Example 3

The modulator of Example 2 can further be optimized by tuning the refractive indexes of the prism and the surrounding medium, and by tuning the angle of incidence. For instance, attenuation can be further increased by replacing the silicon substrate with quartz and setting the angle of incidence to be close to the critical angle for s-polarization (about 30°). It is estimated that an attenuation of 99.5% can be achieved with a sheet conductivity of about 4.7 mS.

Example 4

An optically controlled modulator similar to that shown in FIG. 6 has been constructed. In this example, silicon was used as tunable conductive layer 104, and a diode laser with 450 nm central wavelength was used as light source 602. AR coating 606 was tuned to maximize transmission of the diode laser light.

Figure 14A:
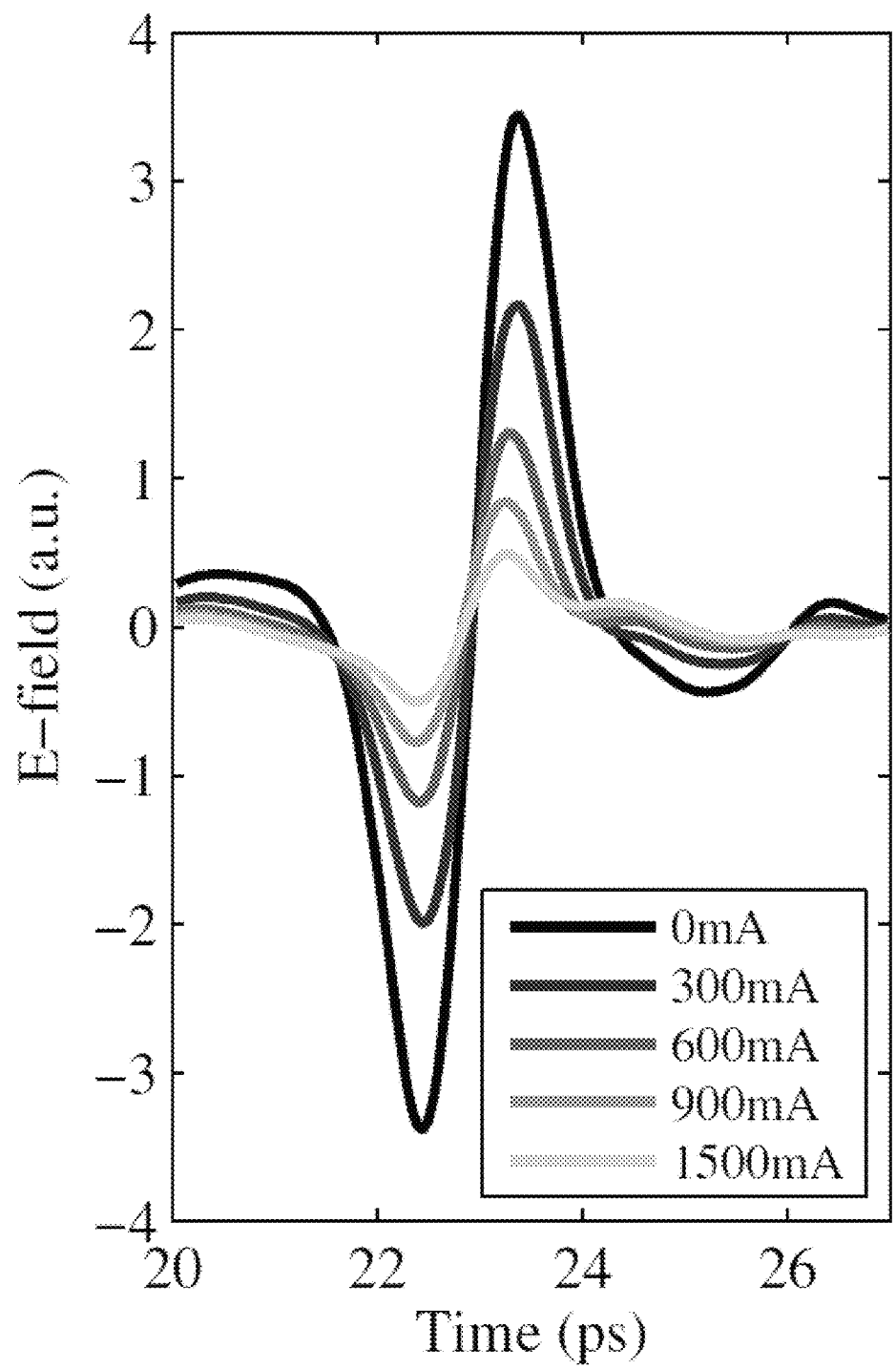
FIGS. 14A and 14B show graphs of experimental results obtained for a device according to another embodiment of the present invention.
Figure 14B:
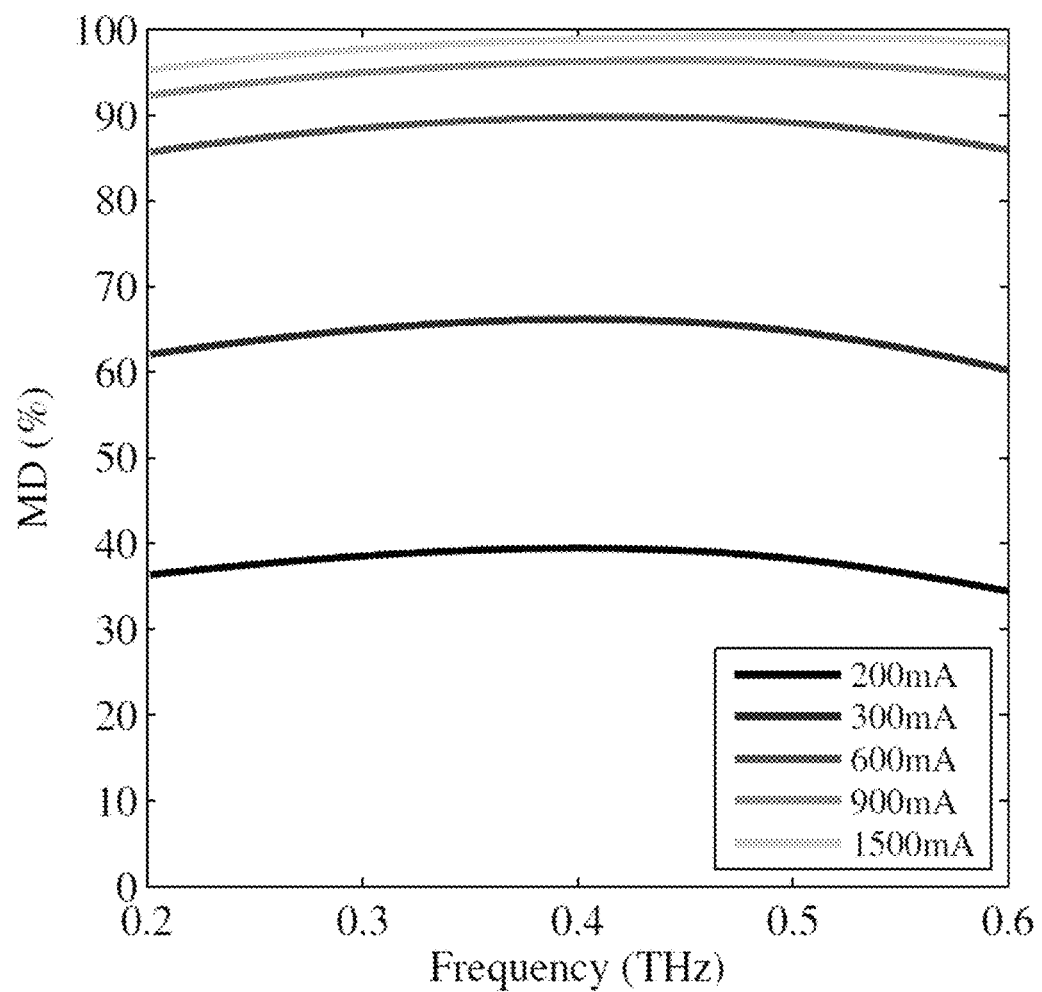

FIG. 14A shows the evolution of the time domain waveform as the laser diode current is increased from 0 mA to 1500 mA in the example device. FIG. 14B shows the modulation depth as a function of frequency for various laser diode currents. As can be seen in FIG. 14B, as the diode current of the laser is increased from 0 mA to 1500 mA, the modulation depth MD of the reflected terahertz beam increases to over 99% across the frequency region. The roll-off at low frequencies is a result of the larger size of the low frequency terahertz light compared to the excitation laser spot.

This optically controlled modulator has also been observed to be controllable using incoherent light, such as an array of light-emitting diodes; use of coherent light is not required. The excitation frequencies can be modified; those skilled in the art with access to the present disclosure will understand that any frequency can be used as long as the photon energy of the excitation light exceeds the bandgap of tunable conductive layer 104.

Further Embodiments

While the invention has been described with respect to specific embodiments, one skilled in the art will recognize that numerous modifications are possible. For example, the materials and fabrication techniques described herein are for purposes of illustration; other materials and techniques can be substituted. Performance can be optimized by tuning the refractive indexes of the prism and the surrounding medium, and by tuning the angle of incidence.

Conductivity of a tunable conductive layer can be controlled using a variety of optical and electrical mechanisms, including but not limited to the examples described above. Other control mechanisms can exploit other environmental conditions (e.g., temperature and/or pressure) that can produce a variation in conductivity of a material.

Thus, although the invention has been described with respect to specific embodiments, it will be appreciated that the invention is intended to cover all modifications and equivalents within the scope of the following claims.

What is claimed is:

1. A modulator for a light beam, the modulator comprising:
    a prism having a first surface to receive a light beam, a second surface to provide total internal reflection of the light beam, and a third surface to permit the light beam to exit the prism;
    a tunable conductive layer disposed on the second surface of the prism such that a reflectivity of the second surface is a function of an electrical conductivity of the tunable conductive layer; and
    a control mechanism to dynamically control the electrical conductivity of the tunable conductive layer and thereby control the reflectivity of the second surface of the prism.

2. The modulator of claim 1 wherein the light beam has a frequency in the range from about 0.1 THz to about 300 THz.

3. The modulator of claim 1 wherein the tunable conductive layer modifies an intensity of the light beam by an amount that depends on the electrical conductivity of the tunable conductive layer.

4. The modulator of claim 1 wherein the tunable conductive layer modifies a phase of the light beam by an amount that depends on the electrical conductivity of the tunable conductive layer.

5. The modulator of claim 4 wherein the amount of the phase modification also depends on a polarization state of the light beam.

6. The modulator of claim 5 wherein, for a first conductivity of the tunable conductive layer, the phase modification provides a quarter wave phase difference between s-polarized and p-polarized light and, for a second conductivity of the tunable conductive layer, the phase modification provides a zero phase difference between s-polarized and p-polarized light.

7. The modulator of claim 5 wherein, for a first conductivity of the tunable conductive layer, the phase modification provides a half wave phase difference between s-polarized and p-polarized light and, for a second conductivity of the tunable conductive layer, the phase modification provides a zero phase difference between s-polarized and p-polarized light.

8. The modulator of claim 1 wherein the electrical conductivity of the tunable conductive layer is spatially controllable such that the electrical conductivity is spatially modulated.

9. The modulator of claim 1 wherein the electrical conductivity of the tunable conductive layer depends on a frequency of the received light beam.

10. The modulator of claim 9 wherein the dependence of the electrical conductivity on frequency is such that light above a cutoff frequency is substantially attenuated while light below the cutoff frequency is not substantially attenuated.

11. The modulator of claim 9 wherein the dependence of the electrical conductivity on frequency is such that light below a cutoff frequency is substantially attenuated while light above the cutoff frequency is not substantially attenuated.

12. The modulator of claim 1 wherein the control mechanism includes:
    a plurality of electrodes connected to the tunable conductive layer,
    wherein the electrical conductivity of the tunable conductive layer is controlled by applying an electrical potential to one or more of the electrodes.

13. The modulator of claim 1 wherein the control mechanism includes:
an optical pump light source arranged to direct pumping light from outside the prism toward the tunable conductive layer,
wherein the electrical conductivity of the tunable conductive layer is controlled by optical pumping of the tunable conductive layer.

14. The modulator of claim 13 wherein the pumping light is spatially modulated and the electrical conductivity of the tunable conductive layer is correspondingly spatially modulated.

15. The modulator of claim 13 further comprising:
an antireflective layer disposed on the tunable conductive layer.

16. The modulator of claim 1 wherein the tunable conductive layer comprises graphene.

17. The modulator of claim 1 wherein the tunable conductive layer comprises a graphene monolayer disposed on a substrate.

18. The modulator of claim 17 wherein the substrate comprises a silicon dioxide insulating layer.

19. The modulator of claim 17 wherein the substrate comprises a silicon layer and a silicon dioxide insulating layer.

20. The modulator of claim 17 further comprising an ion-gel layer disposed over the graphene monolayer.

21. The modulator of claim 1 wherein the tunable conductive layer comprises a material selected from a group consisting of silicon, vanadium dioxide, and gallium arsenide.

22. The modulator of claim 1 wherein the tunable conductive layer includes a metamaterial.

23. The modulator of claim 22 wherein the metamaterial includes one or more of:
an array of split ring resonators; or
a metallic grating.

24. The modulator of claim 1 wherein the prism comprises one or more of:
quartz;
a polymer that is optically transparent at a frequency of the light beam;
sapphire; or
silicon.

25. The modulator of claim 1 wherein the prism is triangular.

* * * * *